United States Patent
Yoshida et al.

(10) Patent No.: US 6,316,658 B1
(45) Date of Patent: Nov. 13, 2001

(54) N-CYCLOPROPYL-2-DIFLUOROMETHOXY-3-HALOGENOANILINES AND INTERMEDIATES FOR THE PREPARATION THEREOF

(75) Inventors: Yasuo Yoshida; Hiroaki Takeuchi, both of Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/529,280

(22) PCT Filed: Aug. 11, 1999

(86) PCT No.: PCT/JP99/04343

§ 371 Date: Apr. 11, 1999

§ 102(e) Date: Apr. 11, 1999

(87) PCT Pub. No.: WO00/09472

PCT Pub. Date: Feb. 24, 2000

(30) Foreign Application Priority Data

Aug. 12, 1998 (JP) .................................................. 10-228062

(51) Int. Cl.$^7$ ........................ C07C 205/37; C07C 217/84
(52) U.S. Cl. ............................. 560/44; 564/442; 568/588
(58) Field of Search ............................. 560/44; 564/442; 568/588

(56) References Cited

FOREIGN PATENT DOCUMENTS

| 57-81449 A | 5/1982 | (JP) . |
|---|---|---|
| 61-22079 A | 1/1986 | (JP) . |
| 6-116241 A | 4/1994 | (JP) . |

OTHER PUBLICATIONS

Krishnan, R. et al. "Synthesis and antibacterial activity of 6–difluoromethoxy–7–piperazinyl–3–quinolinecarboxylic acid derivatives" J. Pharm. Sci. 1988, vol. 77, No. 5, p458–460.

*Primary Examiner*—Richard L. Raymond
(74) *Attorney, Agent, or Firm*—Kubovcik & Kubovcik

(57) ABSTRACT

N-Cyclopropyl-2-difluoromethoxy-3-halogenoanilines which serve as important intermediates in the preparation of quinolonecarboxylic acids useful as synthetic antimicrobial agents from industrially inexpensive and easily available raw materials; and intermediates for the preparation thereof. Specifically, compounds represented by the general formula (1), (2) and (3),

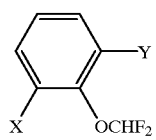
(1)

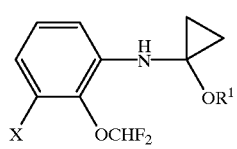

(2)

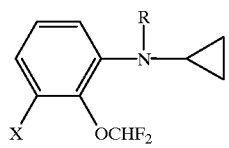

(3)

wherein X is halogeno; and Y is nitro or amino, (2) wherein X is halogeno; and $R^1$ is lower alkyl, (3) wherein X is halogeno; and R is hydrogen or —CH=C$(CO_2R^2)_2$, $R^2$ being lower alkyl.

3 Claims, No Drawings

N-CYCLOPROPYL-2-DIFLUOROMETHOXY-3-HALOGENOANILINES AND INTERMEDIATES FOR THE PREPARATION THEREOF

TECHNICAL FIELD

The present invention relates to an N-cyclopropyl-2-difluoromethoxy-3-halogenoaniline and an intermediate used for production thereof.

BACKGROUND ART

In an international publication, WO 97/29102 is disclosed a quinolonecarboxylic acid having a cyclopropyl group at the 1-position, an isoindolinyl group at the 7-position and a difluoromethoxy group at the 8-position, which is a synthetic antibacterial agent.

However, in the production method of the quinolonecarboxylic acid described in the above laid-open patent publication, 2,6-difluoroaniline which is difficult to synthesize and procure industrially, must be used as a starting material; many steps are employed; explosive sodium azide is used; and a diazotization step of low productivity is included. Thus, in carrying out the industrial production of the quinolonecarboxylic acid according to above method, there have been many problems in cost and safety.

The present inventors made studies on the intermediate for the quinolonecarboxylic acid and the process for production thereof. As a result, it was found out that by using a 2-difluoromethoxy-3-halognonitrobenzene (which is a novel substance) as a raw material, reducing the compound to corresponding aniline, subjecting the aniline to cyclopropylation to synthesize an N-cyclopropylaniline, and reacting it with a dialkyl alkoxymethylenemalonate typified by diethyl ethoxymethylenemalonate, a corresponding adduct was formed.

By subjecting the adduct to a ring-closing reaction according to a known method, there can be easily derived a precursor of the above-mentioned quinolonecarboxylic acid, i.e. an alkyl 1-cyclopropyl-4-oxo-7-halogeno-8-difluoromethoxy-3-carboxylate. Therefore, it was confirmed that the above-mentioned intermediates (2-difluoromethoxy-3-halogenonitrobenzene, corresponding aniline and N-cyclopropylaniline) are important novel compounds in producing the above quinolonecarboxylic acid derivative at a low cost according to an industrially satisfactory method and are all easily synthesized industrially. Thus, the present invention has been completed.

DISCLOSURE OF THE INVENTION

The present invention provides a difluoromethoxybenzene derivative represented by the following formula (1):

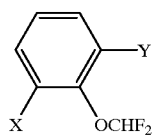

(1)

wherein X is a halogen atom and Y is a nitro group or an amino group.

The present invention further provides an N-(1-alkoxycyclopropyl)-2-difluoromethoxy-3-halogenoaniline derivative represented by the following formula (2):

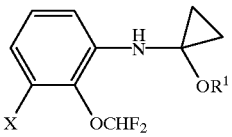

(2)

wherein X is a halogen atom and $R^1$ is a lower alkyl group; and an N-cyclopropyl-2-difluoromethoxy-3-halogenoaniline derivative represented by the following formula (3):

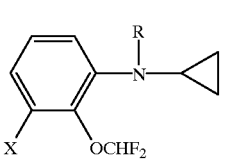

(3)

wherein X is a halogen atom and R is a hydrogen atom or a 2,2-di(alkoxycarbonyl)ethylene group represented by the following formula (4):

$$—CH═C(CO_2R^2)_2 \qquad (4)$$

(wherein $R^2$ is a lower alkyl group).

BEST MODE FOR CARRYING OUT THE INVENTION

The present invention is described in detail below.

To obtain the final objective compound of the present invention, first, one of the objective compounds of the present invention, i.e. a 2-difluoromethoxy-3-halogenonitrobenzene [a compound of the formula (1) wherein Y is a nitro group] is synthesized. As the raw material therefor, there can be used a 2-halogenophenol of good industrial availability such as 2-chlorophenol, 2-bromophenol, 2-iodophenol or the like. By nitrating the 2-halogenophenol according to a known method, there is obtained a 2-halogeno-6-nitrophenol such as 2-cloro-6-nitrophenol, 2-bromo-6-nitrophenol, 2-iodo-6-nitrophenol or the like.

In the above nitration, position isomers of nitro group are formed. However, an objective 2-halogeno-6-nitrophenol can be easily isolated at a high purity by using a purification means such as steam distillation, recrystallization or the like.

The 2-halogeno-6-nitrophenol can also be obtained by using an o-nitrophenol as a starting material and subjecting it to halogenation. Various other methods can also be used. In the present invention, there is no restriction as to the method for obtaining the 2-halogeno-6-nitrophenol.

Next, the 2-halogeno-6-nitrophenol is reacted with a difluoromethylation agent, for example, chlorodifluoromethane, whereby can be obtained a 2-difluoromethoxy-3-halogenonitrobenzene [a compound of the formula (1) wherein Y is a nitro group], such as 2-difluoromethoxy-3-chloronitrobenzene, 2-difluoromethoxy-3-bromonitrobenzene, 2-difluoromethoxy-3-iodonitrobenzene or the like.

The above difluoromethylation can be conducted by reacting the 2-halogeno-6-nitrophenol with a difluoromethylation agent (e.g. chlorodifluoromethane) in the presence of a base. In this reaction, there may be used a solvent such as halogenated solvent (e.g. dichloromethane or dichloroethane), ether type solvent (e.g. 1,4-dioxane, tetrahydrofuran, dimethoxyethane or diethylene glycol dimethyl ether), aprotic polar solvent (e.g. dimethylformamide, dimethylacetamide or dimethyl sulfoxide) or the like.

The temperature of the difluoromethylation must be room temperature or higher. The reaction can be conducted in a temperature range up to the boiling point of the solvent used, at ordinary pressure. The reaction may be conducted under a pressure which is generated spontaneously in a closed vessel. The temperature is specifically from room temperature to 150° C., preferably from 50 to 120° C.

The amount of the difluoromethylation agent (e.g. chlorodifluoromethane) used is 1 to 20 moles, preferably 1 to 5 moles per mole of the 2-halogeno-6-nitrophenol. The base used can be exemplified by inorganic bases such as sodium hydroxide, potassium hydroxide, sodium carbonate, potassium carbonate and the like. Of these, sodium hydroxide, potassium hydroxide or the like is preferred.

Incidentally, the difluoromethylation may be conducted in the presence of a phase transfer catalyst such as tetra-n-butylammonium bromide, benzyltrimethylammonium chloride or the like.

Next, the above-obtained 2-difluoromethoxy-3-halogenonitrobenzene is reduced to obtain a 2-difluoromethoxy-3-halogenoaniline [a compound of the formula (1) wherein Y is an amino group], which is one objective compound of the present invention. A known technique can be used in this reduction reaction.

There can be specifically used reduction using a metal (e.g. iron powder, zinc or tin); catalytic reduction; reduction using a metal hydride (e.g. aluminum lithium hydride or sodium boron hydride); or reduction using a sulfur compound (e.g. sodium hydrosulfide or sodium dithionite). Reduction using an iron powder is preferred.

The above-obtained 2-difluoromethoxy-3-halogenoaniline is subjected to cyclopropylation, whereby can be synthesized an N-cyclopropoyl-2-difluoromethoxy-3-halogenoaniline [a compound of the formula (3) wherein R is a hydrogen atom], which is one objective compound of the present invention. The cyclopropylation can be conducted by, as reported in J. Chem. Soc. Chem. Comm. 897 (1987), reacting the 2-difluoromethoxy-3-halogenoaniline with 1-bromo-1-ethoxycyclopropane and then reacting the reaction product with sodium boron hydride and boron trifluoride etherate.

Or, the cyclopropylation may be conducted by, as described in JP-A-10-87584, reacting the 2-difluoromethoxy-3-halogenoaniline with a 1-alkoxy-1-trimethylsilyloxy-cyclopropane (e.g. 1-ethoxy-1-trimethylsilyloxycyclopropane) in the presence of an organic acid (e.g. formic acid or acetic acid) or an inorganic acid (e.g. hydrochloric acid or sulfuric acid) in a straight chain or branched chain alcohol type solvent having 1 to 6 carbon atoms, and then reducing the reaction product with, for example, sodium boron hydride, preferably in the presence of boron trifluoride etherate or the like.

Incidentally, when there is adopted, for example, the above-mentioned reaction of 2-difluoromethoxy-3-halogenoaniline with 1-alkoxy-1-trimethylsilyloxycyclopropane (e g. 1-ethoxy-1-trimethylsilyloxycyclopropane), there is derived an N-(1-alkoxycyclopropyl)-2-difluoromethoxy-3-halogenoaniline derivative represented by the formula (2):

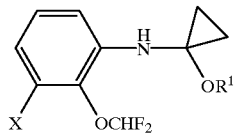

(2)

which is one objective compound of the present invention.

In the above formula (2), X is a halogen atom, and $R^1$ is a lower alkyl group, specifically a straight chain, branched chain or alicyclic alkyl group having 1 to 6 carbon atoms. This $R^1$ may be converted into an alkyl group derived from the solvent used, when there occurs solvent exchange in the reaction between 2-difluoromethoxy-3-halogenoaniline and 1-alkoxy-1-trimethylsilyloxycyclopropane.

The thus-obtained N-cyclopropyl-2-difluoro-methoxy-3-halogenoaniline can be converted, by reaction with an dialkyl alkoxymethylenemalonate typified by diethyl ethoxymethylenemalonate, into a dialkyl N-cyclopropylanilinomethylenemalonate, i.e. a compound of the formula (3) wherein R is a residue represented by the following formula (4):

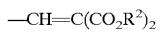  (4)

which is one objective compound of the present invention. In this reaction, dealcoholation takes place simply by mixing and heating the N-cyclopropyl-2-difluoromethoxy-3-halogenoaniline and the dialkyl alkoxymethylenemalonate, and an objective compound can be obtained at a high yield.

In the above formula (4), $R^2$ is a lower alkyl group, specifically a straight chain or branched chain alkyl group having 1 to 6 carbon atoms. Therefore, as the dialkyl alkoxymethylenemalonate usable in the above reaction, there can be mentioned, for example, diethyl ethoxymethylenemalonate, diethyl methoxymethylenemalonate, dimethyl methoxymethylenemalonate, diethyl propoxymethylenemalonate, diethyl butoxymethylenemalonate, dimethyl ethoxymethylenemalonate, dipropyl methoxymethylenemalonate, dimethyl propoxymethylenemalonate and dibutyl butoxymethylenemalonate.

In the above reaction, the amount of the dialkyl alkoxymethylenemalonate used can be, for example, 1.0 to 10.0 moles, preferably 1.0 to 15.0 moles per mole of the N-cyclopropyl-2-difluoromethoxy-3-halogenoaniline.

The thus-obtained dialkyl N-cyclopropylanilinomethylenemalonate [a compound of the formula (3) wherein R is a residue represented by the formula (4)] is easily subjected to ring closure by reaction with polyphosphoric acid, polyphosphoric acid ester or the like according to a known method, and can be easily converted into a 1-cyclopropyl-4-oxo-7-halogeno-8-difluoromethoxy-3-carboxylic acid ester which is an important precursor for a synthetic antibacterial agent having an isoindolinyl group at the 7-position.

EXAMPLES

Next, the present invention is described in more detail by way of Examples.

Reference Example 1

Synthesis of 2-halogeno-6-nitrophenol 51.9 g (0.3 mol) of 2-bromophenol and 300 ml of acetic acid were fed into a 1-liter four-necked flask provided with a reflux condenser, a stirrer and a thermometer. Thereto was dropwise added 29.7 g (0.33 mol) of 70% nitric acid at a temperature of 15° C. or below, with ice-cooling. The reaction mixture was stirred at a temperature of 10° C. or below for 1 hour and poured into 600 ml of water. The mixture was subjected to extraction with 400 ml of ether. The ether layer was washed with 150 ml of water. The ether layer was subjected to distillation. The residue was transferred into a 1-liter flask provided with a stirrer and a distillation apparatus. Azeotropic distillation was conducted while water was added gradually. The amount of water required for azeotropic distillation was 2,100 ml. The distillate obtained was subjected to extraction two times using 500 ml of ether. The ether layer was dried over anhydrous sodium sulfate and subjected to distillation to remove ether. The resulting crude product was mixed with 10 ml of ethanol. The mixture was heated and then allowed to cool. The formed crystals were collected by filtration and then dried to obtain 22.3 g of 2-bromo-6-nitrophenol (yield: 34.1%, purity: 99.6%).

Example 1

Into a 200-ml four-necked flask provided with a reflux condenser, a stirrer and a thermometer were fed 4.36 g (0.02 mol) of 2-bromo-6-nitrophenol, 16.7 g (0.1 mol) of 24% sodium hydroxide, 20 ml of 1,4-dioxane and 7 ml of water. The mixture was heated to 80° C. The mixture was stirred at that temperature for 11 hours with heating while chlorodifluoromethane (flon 22) was blown thereinto from a bomb. The reaction mixture was cooled and then subjected to extraction two times each using 20 ml of ether. The ether layer was washed with 20 ml of 12% sodium hydroxide and then with the same volume of water. Then, the ether layer was dried over anhydrous sodium sulfate and then subjected to distillation to obtain 1.79 g of 3-bromo-2-difluoromethoxynitrobenzene (yield: 33.4%, purity: 98.8%). To the sodium hydroxide washing was added hydrochloric acid to make the washing acidic, and the resulting precipitate was subjected to extraction with ether, to recover 2.2 g of unreacted 2-bromo-6-nitrophenol (recovery ratio: 50%).

Data obtained for 3-bromo-2-difluoromethoxynitrobenzene

Melting point: 43 to 45° C.

IR (KBr, cm$^{-1}$): 1520, 1350 (NO$_2$), 1040–1160 (CF$_2$)

Mass (m/e): 267, 269 (1:1, M$^+$), 217, 219 (M$^+$—CF$_2$), 200, 202 (M$^+$—OCHF$_2$)

$^1$H-NMR (σ, CDCl$_3$): 6.60 (t, 1H, J=74 Hz, OCHF$_2$), 7.1–8.1(m, 3H, aromatic protons)

Example 2

Into a 100-ml four-necked flask provided with a reflux condenser, a stirrer and a thermometer were fed 0.95 g (17.0 mmol) of an iron powder, 0.11 g (1.0 mmol) of 98% sulfuric acid, 15 ml of water and 1.62 g (6.0 mmol) of 3-bromo-2-difluoromethoxynitrobenzene. The mixture was heated on an oil bath and refluxed for 2 hours. After the completion of a reaction, azeotropic distillation was conducted while 220 ml of water was added gradually. The distillate was subjected to extraction two times each using 100 ml of ether. The ether layer was dried over anhydrous sodium sulfate and then subjected to distillation. The residue was distilled under vacuum to obtain 0.94 g of 3-bromo-2-difluoromethoxyaniline (yield: 65.4%, purity: 98.5%).

Data obtained for 3-bromo-2-difluoromethoxyaniline

Boiling point: 135 to 140° C./9 mmHg (micro distillation, external temperature)

IR (neat, cm$^{-1}$): 3200–3500 (NH$_2$), 1000–1160 (CF$_2$)

Mass (m/e): 237, 239 (1:1, M$^+$), 197, 199 (M$^+$—2HF), 187, 189 (M$^+$—CF$_2$)

$^1$H-NMR (σ, CDCl$_3$): 3.6–4.7 (broad s, 2H, NH$_2$), 6.46 (t, 1H, J=75 Hz, OCHF$_2$), 6.5–7.2 (m, 3H, aromatic protons)

Example 3

Into a 50-ml three-necked flask provided with a reflux condenser, a magnetic stirrer and a thermometer were fed 0.88 g (3.7 mmol) of 3-bromo-2-difluoromethoxyaniline, 0.75 g (4.4 mmol) of 1-ethoxy-1-trimehtylsilyloxycyclopropane, 0.67 g (11.2 mmol) of acetic acid and 8 ml of methanol. The mixture was heated on an oil bath and refluxed for 6 hours. Thereto was added 0.32 g (1.9 mmol) of 1-ethoxy-1-trimethylsilyloxycyclopropane, followed by refluxing for 12 hours. After completion of the reaction, methanol and acetic acid were removed by distillation under vacuum using a rotary evaporator, to obtain, as an oily substance, 1.00 g of 1-(3-bromo-2-difluoromethoxy) anilino-1-methoxycyclopropane (yield: 87.8%, purity: 92.3%).

Data obtained for 1-(3-bromo-2-difluoromethoxy) anilino-1-methoxycyclopropane

Mass (m/e): 307, 309 (1:1, M$^+$), 257, 259 (M$^+$—CF$_2$)

$^1$H-NMR (σ, CDCl$_3$): 0.7–1.3 (4H, m, —CH$_2$CH$_2$), 3.26 (3H, S, OCH$_3$), 5.1–5.8 (broad S, 1H,NH), 6.48 (t, 1H, J=75 Hz, OCHF$_2$), 6.7–7.4 (m, 3H, aromatic protons)

Example 4

Into a 50-ml three-necked flask provided with a reflux condenser, a magnetic stirrer and a thermometer were fed 0.16 g (4.2 mmol) of sodium boron hydride and 8 ml of anhydrous tetrahydrofuran. The flask inside was purged with nitrogen, and the flask contents were ice-cooled. Thereto was dropwise added 0.6 g (4.2 mmol) of boron trifluoride-tetrahydrofuran complex at 5° C. The reaction mixture was stirred at 5° C. for 2 hours. Thereto was dropwise added, at the same temperature, a solution of 1.00 g (3.3 mmol) of the crude 1-(3-bromo-2-difluoromethoxy)anilino-1-methoxycyclopropane obtained in Example 3, dissolved in 2 ml of tetrahydrofuran. The mixture was heated, and stirred at room temperature for 1 hour and then at 60° C. for 2.5 hours. Thereinto were fed 0.1 g (2.8 mmol) of sodium boron hydride and 0.4 g (2.8 mmol) of boron trifluoride-tetrahydrofuran complex in this order, followed by stirring at 60° C. for 2 hours. The reaction mixture was cooled and poured into water. The mixture was subjected to extraction two times each using 10 ml of ether. The residue was subjected to distillation under vacuum to obtain 0.39 g of N-cyclopropyl-2-difluoromethoxy-3-bromo-aniline (yield: 42.3%, purity: 96.4%).

Data obtained for N-cyclopropyl-2-difluoromethoxy-3-bromo-aniline

Boiling point: 145–150° C./5 mmHg (micro distillation, external temperature)

IR (neat, cm$^{-1}$): 3450 (NH), 1000–1160 (CF$_2$)

Mass (m/e): 277, 279 (1:1, M$^+$), 210, 212 (M$^+$—CHF$_2$O)

$^1$H-NMR (σ, CDCl$_3$): 0.4–0.9 (4H, m, —CH$_2$CH$_2$), 2.1–2.7 (1H, m, NCH), 4.5–4.8 (broad s, 1H, NH), 6.41 (t, 1H, J=75 Hz, OCHF$_2$), 6.7–7.4 (m, 3H, aromatic protons)

Example 5

Into a 25-ml round-bottomed flask provided with a distillation apparatus and a magnetic stirrer were fed 0.28 g (1.0 mmol) of N-cyclopropyl-2-difluoromethoxy-3-bromoaniline obtained in Example 4 and 1.08 g (5.0 mmol) of diethyl ethoxymethylenemalonate. The mixture was stirred with heating on an oil bath of 140° C. for 30 minutes. During the period, ethanol vaporized gradually. The oil bath temperature was increased to 160° C. and stirring was conducted for 1 hour. Then, the same operation was conducted at 180° C. for 4.5 hours. The reaction mixture was cooled and subjected to column chromatography [packing material: Wako Gel C-60, eluent: n-hexane/ethyl acetate (8:1)] to remove colored substances. Then, the solvent was removed by distillation to obtain 1.3 g of a light yellow oily substance. The oily substance was transferred into a micro distillation apparatus and heated under vacuum (1 mmHg) on an oil bath of 140 to 150° C. to distil off unreacted diethyl ethoxymethylenemalonate, whereby was obtained, as an oily residue, 180 mg of diethyl N-cyclopropyl-2-difluoromethoxy-3-bromoanilinomethylenemalonate (yield: 40.2%, purity: 97.6%).

Data obtained for diethyl N-cyclopropyl-2-difluoromethoxy-3-bromoanilinomethylenemalonate Mass (m/e): 449, 447 (1:1, $M^+$)

$^1$H-NMR ($\sigma$, $CDCl_3$): 0.6–0.8 (4H, m, $—CH_2CH_2$), 1.08 (3H, t, J=7.0 Hz, $CH_3$), 1.25 (t, 3H, J=7.0 Hz, $CH_3$), 3.71 (q, 2H, J=7.0 Hz, $CH_2$), 4.10 (q, 2H, J=7.0 Hz, $CH_2$), 6.65 (t, 1H, J=73 Hz, $CHF_2$), 7.64 (s, 1H, C=CH), 6.9–7.5 (m, 2H, aromatic protons)

Example 6

Into a 1-liter four-necked flask provided with a reflux condenser, a stirrer and a thermometer were fed 53.0 g (0.24 mol) of 2-bromo-6-nitrophenol, 40.5 g (0.49 mol) of 48% sodium hydroxide, 240 ml of 1,3-dimethylimidazolidine-2-one and 40.5 g of water. The mixture was heated to 80° C. and stirred at the same temperature for 1.5 hours with heating while chlorodifluoromethane (flon 22) was blown thereinto from a bomb. Then, while 20.0 g of 48% sodium hydroxide was added in seven portions, blowing of flon gas was continued at the same temperature for 7.5 hours. The total amount of flon gas blown was 242.3 g (2.80 mol). The reaction mixture was cooled. Thereto were added 26.0 g of 48% sodium hydroxide, 1 liter of water and 500 ml of ether, and extraction and layer separation was conducted. The organic layer was separated, and the water layer was subjected to reextraction using 500 ml of ether. The ether layers were combined and washed with 500 ml of water two times. The resulting organic layer was dried over anhydrous sodium sulfate and subjected to distillation to remove the solvent and obtain 45.4 g of 3-bromo-2-difluoromethoxynitrobenzene (yield: 70.6%, purity: 98.1%).

Example 7

Into a 300-ml four-necked flask provided with a reflux condenser, a stirrer and a thermometer were fed 6.56 g of an iron powder, 0.49 g (4.7 mmol) of 95% sulfuric acid and 50 ml of water. The mixture was heated to 80° C. on an oil bath. Thereto was slowly added, at 80 to 85° C., 12.54 g (0.047 mol) of 3-bromo-2-difluoromethoxynitrobenzene. The temperature was increased and refluxing was conducted at 100° C. for 2 hours with heating. After completion of the reaction, azeotropic distillation was performed while 200 ml of water was added gradually. The distillate was subjected to extraction two times each using 30 ml of dichloromethane. The organic layer was dried over anhydrous sodium sulfate and subjected to distillation to remove the solvent and obtain 8.09 g of 3-bromo-2-difluoromethoxyaniline (yield: 72.4%, purity: 99.7%).

Example 8

Into a 200-ml three-necked flask provided with a reflux condenser, a magnetic stirrer and a thermometer were fed 8.09 g (0.034 mol) of 3-bromo-2-difluoromethoxyaniline, 8.54 g (0.049 mol) of 1-ethoxy-1-trimethylsilyloxycyclopropane, 6.54 g (0.109 mol) of acetic acid and 36 ml of methanol. The mixture was heated on an oil bath and refluxed for 10 hours. After the completion of a reaction, methanol and acetic acid were removed by distillation under vacuum using a rotary evaporator to obtain, as a light yellow oily substance, 11.48 g of 1-(3-bromo-2-difluoromethoxy)anilino-1-methoxycyclopropane.

Example 9

1.67 g (0.044 mol) of sodium boron hydride and 15 ml of anhydrous tetrahydrofuran were fed into a 200-ml four-necked flask provided with a reflux condenser, a stirrer and a thermometer. The flask inside was purged with nitrogen and the flask contents were ice-cooled. Thereto was dropwise added, at 5° C., 6.22 g (0.044 mmol) of boron trifluoridetetrahydrofuran complex. The reaction mixture was stirred at 0 to 5° C. for 1 hour. Thereto was dropwise added, at 10 to 20° C., a solution of 11.48 g of the crude 1-(3-bromo-2-difluoromethoxy)anilino-1-methoxycyclopropane obtained in Example 8, dissolved in 5 ml of toluene. The mixture was stirred at 50° C. for 2.5 hours and then at 60° C. for 15 hours. N-cyclopropyl-2-difluoromethoxy-3-bromoaniline (an objective compound) was formed by 50.5%.

1.93 g (0.051 mol) of sodium boron hydride and 15 ml of anhydrous tetrahydrofuran were fed into a 50-ml three-necked flask provided with a magnetic stirrer and a thermometer as same as mentioned above. The flask inside was purged with nitrogen and the flask contents were ice-cooled. Thereto was dropwise added, at 5° C., 7.04 g (0.050 mmol) of boron trifluoride-tetrahydrofuran complex. The reaction mixture was stirred at 0 to 5° C. for 1 hour. The resulting mixture was added to the above-obtained reaction mixture, followed by stirring at 60° C. for 24 hours. The reaction mixture was cooled and poured into 200 ml of water. The mixture was stirred at room temperature for 2 hours and then subjected to extraction using 200 ml of ether. The ether layer was dried over anhydrous sodium sulfate and subjected to distillation to remove the solvent and obtain 10.17 g of a colorless oily substance. This substance was subjected to distillation under vacuum to obtain 7.82 g of N-cyclopropyl-2-difluoromethoxy-3-bromoaniline (yield: 82.7% relative to the raw material used in Example 8, purity: 95.4%).

Example 10

Into a 50-ml round-bottomed flask provided with a distillation apparatus and a magnetic stirrer were fed 3.33 g (0.012 mol) of N-cyclopropyl-2-difluoromethoxy-3-bromoaniline and 3.11 g (0.0144 mol) of diethyl ethoxymethylenemalonate. The mixture was stirred on an oil bath at 150° C. for 1.5 hours. During this period, ethanol vaporized gradually. The reaction temperature was increased to 170° C., and stirring was conducted for 13.5 hours while nitrogen gas was blown thereinto. The reaction mixture was cooled to obtain a brown oily substance. This substance was analyzed by gas chromatography. As a result, the substance contained 10.8% (by areal percentage) of diethyl ethoxymethylenemalonate and 86.6% of, as an objective compound, diethyl N-cyclopropyl-2-difluoromethoxy-3-bromoanilinomethylenemalonate.

Reference Example 2

26 g of polyphosphoric acid was fed into a 200-ml four-necked flask provided with a reflux condenser, a stirrer and a thermometer. The mixture was heated to 60° C. Thereto was dropwise added, at 55 to 60° C., the crude diethyl N-cyclopropyl-2-difluoromethoxy-3-bromoanilinomethylenemalonate obtained in Example 10, dissolved in 0.8 g of toluene. The mixture was heated with stirring, and stirred at 90 to 95° C. for 2 hours. The reaction mixture was cooled and poured into 100 ml of water, and the mixture was stirred for 1 hour. The resulting crystals were collected by filtration, washed with water, and dried to obtain 3.98 g of crude crystals. 30 ml of ethanol was added to the crude crystals. The mixture was refluxed with heating, cooled and filtered. The collected substance was dried to obtain 2.12 g of ethyl 7-bromo-1-cyclopropyl-8-difluoromethoxy-4-oxo-1,4-dihydro-3-quinoline-carboxylate (yield: 43.9% relative to the raw material used in Example 10). The melting point was 252.6° C.

The IR and NMR spectrum of the obtained compound agreed with those described in the patent publication, WO 97/29102.

Industrial Applicability

As described above, the present invention provides, from a halogenophenol or a nitrophenol (each is a raw material which is industrially inexpensive and easy to procure), an n-cyclopropyl-2-difluoromethoxy-3-halogenianiline which is a novel substance not described in any literature and which is an important intermediate for producing, industrially and at a low cost, a synthetic antibacterial agent having an isoindolinyl group, a cyclopropyl group and a difluoromethoxy group; and an intermediate used for production thereof.

What is claimed is:

1. A difluoromethoxybenzene derivative represented by the following formula (1):

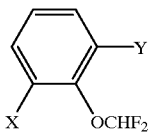

(1)

wherein X is a halogen atom and Y is a nitro group or an amino group.

2. An N-(1-alkoxycyclopropyl)-2-difluoromethoxy-3-halogenoaniline derivative represented by the following formula (2):

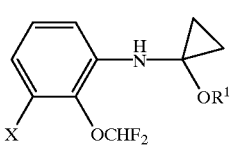

(2)

wherein X is a halogen atom and $R^1$ is a lower alkyl group.

3. An N-cyclopropyl-2-difluoromethoxy-3-halogenoaniline derivative represented by the following formula (3):

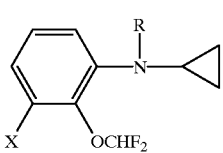

(3)

wherein X is a halogen atom and R is a hydrogen atom or a 2,2-di(alkoxycarbonyl)ethylene group represented by the following formula (4):

—CH=C(CO$_2$R$^2$)$_2$ (4)

(wherein $R^2$ is a lower alkyl group).

* * * * *